(12) United States Patent
Croce et al.

(10) Patent No.: US 7,381,225 B2
(45) Date of Patent: Jun. 3, 2008

(54) REINFORCEMENT PARIETAL PROSTHESIS AND METHOD OF PRODUCING THE SAME

(75) Inventors: Enrico Croce, Cusano Milanino (IT); Stefano Olmi, Milan (IT)

(73) Assignee: Angiologica B.M. S.R.L., Martino Siccomario (IT)

(*) Notice: Subject to any disclaimer, the term of this patent is extended or adjusted under 35 U.S.C. 154(b) by 573 days.

(21) Appl. No.: 11/009,947

(22) Filed: Dec. 10, 2004

(65) Prior Publication Data

US 2005/0165425 A1   Jul. 28, 2005

(30) Foreign Application Priority Data

Dec. 12, 2003   (IT)   .......................... MI2003A2448

(51) Int. Cl.
*A61F 2/02*   (2006.01)
(52) U.S. Cl. .................................. 623/23.72
(58) Field of Classification Search ............. 623/23.74, 623/23.76, 23.64, 14.13, 13.11, 11.11, 23.72; 600/37; 606/151, 213
See application file for complete search history.

(56) References Cited

U.S. PATENT DOCUMENTS

| | | | |
|---|---|---|---|
| 3,286,713 A * | 11/1966 | Kurtz et al. | ................. 604/180 |
| 5,697,978 A | 12/1997 | Sgro | |
| 5,716,409 A | 2/1998 | Debbas | |
| 6,174,320 B1 | 1/2001 | Kugel et al. | |
| 6,258,124 B1 | 7/2001 | Darois et al. | |
| 2003/0171823 A1 | 9/2003 | Zotti et al. | |
| 2003/0212460 A1 | 11/2003 | Darois et al. | |
| 2005/0192600 A1* | 9/2005 | Nicolo et al. | ................ 606/151 |

FOREIGN PATENT DOCUMENTS

| | | |
|---|---|---|
| EP | 0 719 527 | 7/1996 |
| EP | 0 827 724 | 3/1998 |
| FR | 2 744 906 | 8/1997 |
| FR | 2 837 091 | 9/2003 |
| WO | 01/85058 | 11/2001 |

OTHER PUBLICATIONS

English Abstract of EP 0 719 527 dated Jul. 3, 1996.
English Abstract of FR 2 744 906 dated Aug. 22, 1997.
English Abstract of FR 2 837 091 dated Sep. 19, 2003.

* cited by examiner

*Primary Examiner*—(Jackie) Tan-Uyen T. Ho
*Assistant Examiner*—Gregory A Anderson
(74) *Attorney, Agent, or Firm*—Ladas and Parry LLP

(57) ABSTRACT

A pre-shaped and self-blocking reinforcement parietal prosthesis for inguinal hernioplastic surgical operations around the spermatic cord, extends along a longitudinal axis and presents a first and second layers respectively provided with a first and a second holes being aligned with each other so as to define an aperture for the spermatic cord, with a first and second outer edges and with a first and second slits, which extend on opposite side with respect to the longitudinal axis and which connect the first and second holes respectively to the first and second outer edges (6, 9).

8 Claims, 2 Drawing Sheets

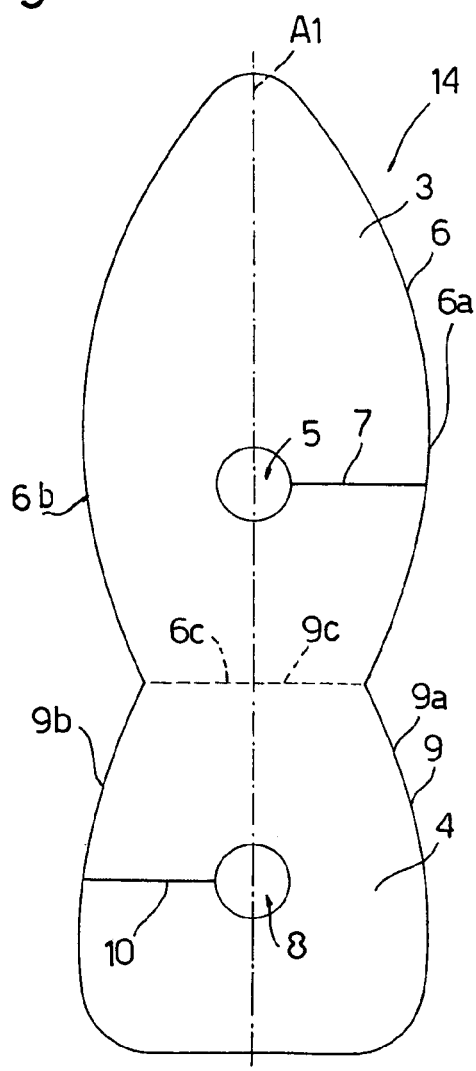
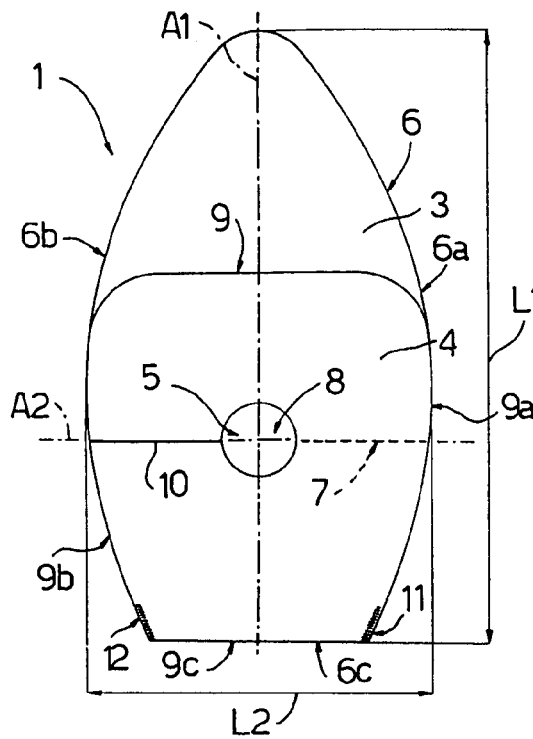
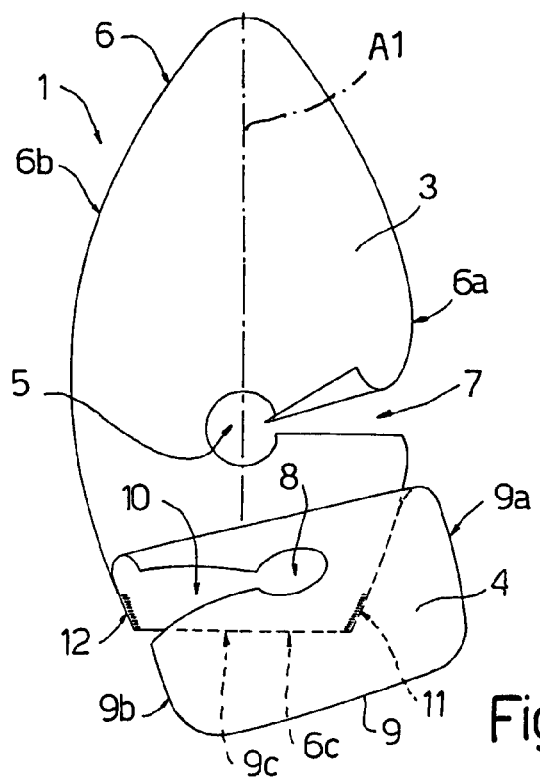

REINFORCEMENT PARIETAL PROSTHESIS AND METHOD OF PRODUCING THE SAME

The present invention relates to a reinforcement parietal prosthesis.

In particular, the present invention relates to a reinforcement parietal prosthesis adapted to be implanted inside the human body during hernioplastic operations in the inguinal region around the spermatic cord.

BACKGROUND OF THE INVENTION

A hernia is defined as a pathology characterised by the protrusion of organs, or their parts, from their natural position through an anomalous aperture in the human tissue. Such a pathology requires a hernioplastic surgical operation during which a reinforcement parietal prosthesis is implanted in the area of the tissue affected by the hernia in order to re-establish the continuity of the tissue and to create a resistance zone. During hernioplastic inguinal surgical operations two substantial problems arise. The first problem relates to the so called relapse or the recurrence of the hernial pathology. The second problem consists in the fact that the hernioplastic operation must not damage the spermatic cord when the reinforcement parietal prosthesis is lodged around the same.

Before carrying out hernioplastic operations, the practice had been to carry out a direct suture of the damaged tissue (Bassini-Shouldice Method). With this operations there has been a very high number (25%) of relapses. To solve this problem surgical techniques have evolved thanks to the implantation of parietal prostheses made up essentially of meshes and placed onto the damaged tissue. The parietal prostheses have helped in lowering the incidence of relapses but have not completely eliminated the problem. In fact, a relapse may be attributed to many factors including the mispositioning of the prosthesis, the fixing suture for the prostheses to the human tissue which can lead to an erroneous tension distribution and the creation of dead spaces and seromas. To solve this problem surgeons have tried to use prostheses of different materials (polypropylene monofilament has proved the most ideal for this purpose), that is, biocompatible meshes with stable physico-chemical and dimensional characteristics such as high resistance to tensile stress, stable biologically, which do not induce inflammatory reaction and which permit a rapid reaction of the fibroblasts, a high capacity to adapt to muscular movements and contractions. An important characteristic turns out to be the pattern of the mesh: in this way it is possible to have a mesh with optimum qualities so as to adapt itself perfectly to the site of the implant. Initially the pattern was made manually in the operating theatre; the next step developed by the manufacturing companies was to reproduce prostheses already preshaped with accurately finished outer edges, fraying- and breaks-free and being of different sizes. The first preshaped prostheses were sutured to the human tissue: one of the disadvantages was the transmitting of tensions between the prosthesis and the human tissue. Then new prostheses and different surgical techniques were approached such as the tension free sutureless mesh and sutureless tension-free repair: this technique requires the use of a prosthesis having a single layer preshaped mesh and provided with a hole and a longitudinal slit to permit the insertion of the spermatic cord into the hole. This prosthesis is not sutured to the human tissue because it remains confined within a well defined anatomical space which constricts movements of the same. The parts of the prosthesis adjacent to the longitudinal slit can be sutured together or left free: in the first case the wings can move and damage the spermatic cord, in the second case the formation of relapses, damage to the spermatic cord and the bending of the parts of the prosthesis along the longitudinal slit are encouraged leading to the formation of dead spaces. This solution does not rule out a possible migration and deformation of the mesh in case that said parts open out if they are free or in case they bend when connected by a suture stitch; nor does it succeed either in completely resolving the problem of the risk of damage to the spermatic cord. Moreover with this solution the risk of the incidence of relapses is not completely eliminated.

To try and solve these problems there has been produced a parietal mesh of reinforcement, subject of the international patent application WO 01/85058 under the title "Double layer anatomic surgical mesh" in the name of the same applicant: it concerns a double layer mesh made up of two superimposed layers with equal coincident holes, and radial divergent slits. The layers present respective external coincident edges joined by a continuous laser welding with the exclusion of the area where there are present the two slits that create two wings initially overlapping, the function of which is to block the mesh at the spermatic cord, avoiding damaging it and without using surgical stitches between the wings. This prosthesis has been designed to be used in those surgical operations where a posterior approach is envisaged: that is the prosthesis is placed in contact with the internal face of the human tissue. Even though this prosthesis has shown itself to be particularly effective from either the point of view of implantation or from that of relapses, it does have the drawback of being particularly expensive due to the high use of materials and of skilled labour and, for this reason, it is not used for more common surgical operation where anterior access is envisaged.

SUMMARY OF THE INVENTION

The object of the present invention is to produce a reinforcement parietal prosthesis which can overcome the abovementioned problems and which, in particular, allows to simplify the hernioplastic surgical operation and to reduce the incidence of relapse phenomena.

According to the present invention there is produced a pre-shaped and self-blocking reinforcement parietal prosthesis for inguinal hernioplastic operations close to the spermatic cord, said prosthesis having an elongated form and extending along a longitudinal axis; the prosthesis comprising a first and a second superimposed layers of mesh material respectively provided with a first and a second holes defining an aperture for accommodating the spermatic cord, with a first and second outer edges and with a first and second slits which connect respectively the first and the second holes to the first and second outer edges; wherein the first and second slits extend from opposite sides with respect to said longitudinal axis.

The above prosthesis succeeds in producing an effective blockage without the need to diffusely bind the layers. In addition this fact also permits a reduction of the dimensions of the second layer, and thus saving material. At the same time the prosthesis proves easy to place during the surgical operation allowing the insertion of one layer at a time around the spermatic cord. Furthermore the prosthesis allows relative movements between the first and second layers.

According to a particular aspect of the present invention the prosthesis a blank, which is folded so as to superimpose the first and the second layers and so that the first and the second holes be substantially coincident.

The present invention furthermore relates to a method of production of a reinforcement parietal prosthesis.

According to the present invention there is provided a method of production of a pre-shaped, self-blocking reinforcement parietal prosthesis for inguinal hernioplastic operations close to the spermatic cord, said prosthesis having an elongated form and extending along a longitudinal axis; wherein the prosthesis comprises a first and a second superimposed layers of mesh material respectively provided with a first and a second holes defining an aperture for accommodating the spermatic cord, with a first and second outer edges and with a first and second slits which connect respectively the first and the second holes to the first and second outer edges; the first and second slits extending from opposite sides with respect to said longitudinal axis; the method comprising the steps of:

cutting a blank extending along said longitudinal axis from a sheet of mesh material for surgery, said blank comprising the first and second layers in a flat planar configuration;

making the first hole in said blank and the first slit which connects said first hole with the first outer edge of the blank;

making the second hole in said blank and the second slit which connects said second hole with the second outer edge of the blank on the side opposite to the first slit with respect to the longitudinal axis; and folding the blank substantially perpendicular to the longitudinal axis so as to superimpose the first and the second layers and to arrange the first and the second holes aligned with each other to define the aperture for said spermatic cord.

Such a method proves to be particularly advantageous in that it simplifies the production operation of the prosthesis, drastically reducing the joining operations which are essentially substituted by an operation of folding the blank.

BRIEF DESCRIPTION OF THE DRAWINGS

To allow a better comprehension of the present invention there will now be described a preferred embodiment as a non limitative example, with reference to the enclosed figures in which FIG. 1 is a plan view of a prosthesis produced according to the invention;

FIG. 2 is a view of the prosthesis in FIG. 1 in a divaricated configuration;

FIG. 3 is a plan view of a blank used in the production method of the prosthesis in FIG. 1;

DETAILED DESCRIPTION OF THE INVENTION

Figure 4:
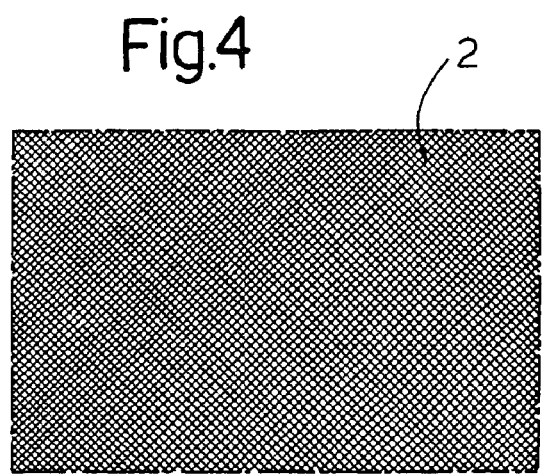
FIG. 4 is a enlarged plan view of the material used in the production of the prosthesis in FIG. 1.

With reference to FIG. 1, with number 1 is indicated a reinforcement parietal prosthesis for hernioplastic surgical operations. The prosthesis 1 is obtained from a material 2 in polypropylene monofilament mesh (FIG. 4). The polypropylene monofilament has shown it self the material most able to satisfy the demands of the parietal prostheses for the following reasons: the polypropylene monofilament shows a high tensile resistance, is biologically stable, is well accepted and does not induce allergic reactions, resists infections precisely due to its monofilament characteristics, does not seem to be carcinogenic, induces a rapid fibroblastic proliferation which brings with it an effective deposit of collagen. These characteristics can only be obtained through adequate mechanical and heat treatment of the material 2 of the polypropylene mesh such as the spinning, the weaving, the pattern, the diameter of the filament, the thickness, the roughness and the size of the pores.

With reference to FIG. 1 the prosthesis 1 presents an elongated, essentially ogival, shape, a longitudinal axis A1 and a transversal axis A2 which is in fact perpendicular to axis A1. The prosthesis 1 is formed by a layer 3 and a layer 4 which are superimposed and joined to each other in a zone arranged on a side of the axis A2 only. The layer 3 presents an elongated form along axis A1, a hole 5, an outer edge 6 and a slit 7 which connects the hole 5 to the edge 6. The layer 4 is smaller in size than layer 3 and presents a hole 8 having the same size as hole 5 and coinciding with the hole 5, an outer edge 9 partly is common with edge 6 and a slit 10 which connects hole 8 with edge 9. Edge 6 has two portions 6a and 6b arranged on opposing sides with respect to axis A1 and facing each other. In the same way edge 9 has two portions 9a and 9b arranged on opposing sides with respect to axis A1 and facing each other. The slits 7 and 10 extend on opposite sides with respect to axis A1 and are essentially aligned to one another and run parallel to axis A2. Substantially the slit 7 connects hole 5 to portion 6a of the edge 6, whilst the slit 10 connects hole 8 to portion 9b of edge 9.

Layer 3 is united to layer 4 along respective portions 6c and 9c of the respective outer edges 6 and 9. These portions 6c and 9c coincide and are perpendicular to axis A1 and parallel to axis A2. Furthermore the layers 3 and 4 are joined together along two segments 11 and 12 on opposite sides with respect to axis A1. The segment 11 is common to the portions 6a and 9a and is adjacent to portions 6c and 9c. Similarly the segment 12 is common to the portions 6b and 9b and is adjacent to portions 6c and 9c. The prosthesis 1 extends for a length L1 in a range of 90 to 140 mm along axis A1 and for a width L2 in a range of 40 to 80 mm along axis A2. The segments 11 and 12 extend for a length equal to about $\frac{1}{10}$ of the length L1.

Figure 5:
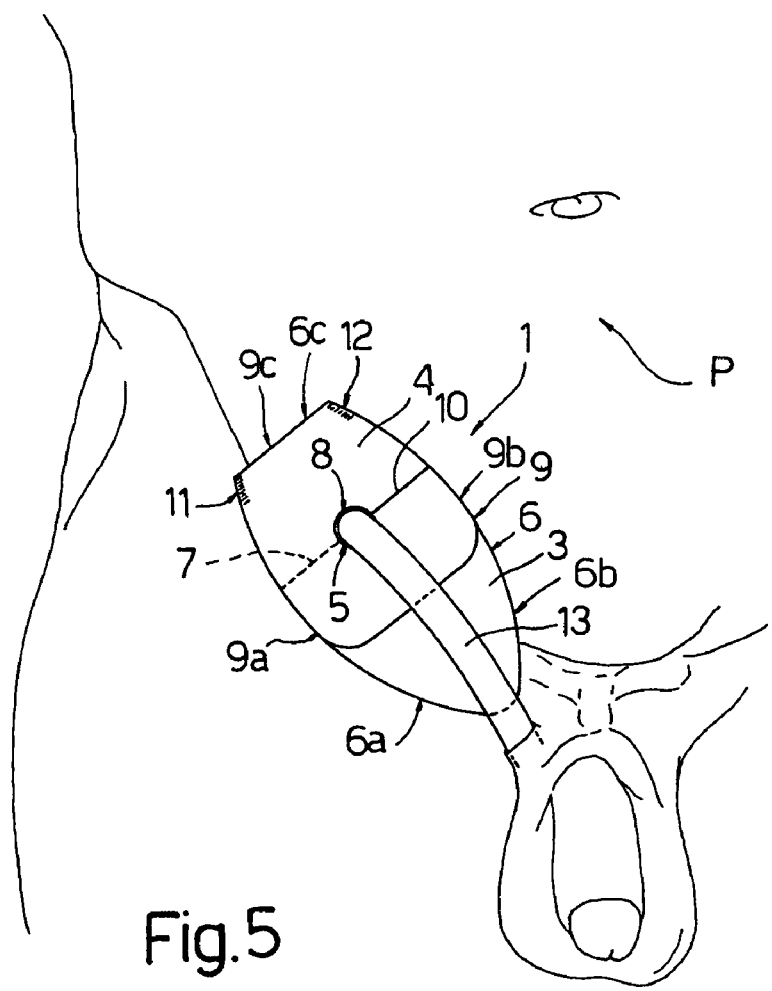
FIG. 5 is a front elevation schematic view which shows the prosthesis in FIG. 1 placed around the spermatic cord of a patient.

With reference to FIG. 5 the hernioplastic surgical operation provides the implant of the prosthesis 1 in a patient P and places the prosthesis 1 with the axis A1 actually coinciding with the inguinal canal and around the spermatic cord of the patient P.

Substantially the holes 5 and 8 define an aperture which is occupied by the spermatic cord 13.

The surgical operation results particularly simplified in so much as the aim is to insert layer 3 around the spermatic cord 13 through the slit 7, and to insert, in turn, layer 4 around the spermatic cord 13 through slit 10 and to place layer 4 on top of layer 3. The prosthesis 1 is self-blocking and it is not necessary to suture together layers 3 and 4. In fact the prosthesis 1 is prevented from moving inside an anatomical space closed by aponeurotic fascial tissues. Furthermore, the sliding of the layers 3 and 4 one over the other until a complete histic unity is achieved allows the prosthesis 1 to adapt perfectly to the anatomical variations of the inguinal region without tractions and tensions which, in the absence of anchorage stitching of the prosthesis 1, reduce the post-operative pain.

The prosthesis 1 can be produced starting from two separated joined together layers. However according to an embodiment of the present invention which is particularly advantageous, the layers 3 and 4 are produced from a single blank 14 of material 2 (FIG. 3). In practice, a blank 2 extending along axis A1 is cut from a sheet of material 2.

The blank 14 comprises layer 3 and layer 4 arranged in a flat configuration and joined together without interruption in the area of rectilinear portions 6c and 9c of the respective edges 6 and 9. In the blank 14 the holes 5 and 8 are made in a symmetrical position with respect to the rectilinear portions 6c and 9c and the slits 7 and 10 are made so as to extend on opposite sides with respect to axis A1.

Then, the blank 14 is folded in the area of portions 6c and 9c so as to place holes s 5 and 8 to coincide with one another. Finally the edge portions 6a and 9a on one side, and 6b and 9b on the other side are joined together along the segments 11 and 12.

According to a not shown embodiment, the slits are not aligned one with the other and lie on lines essentially parallel to each other. According to another not shown embodiment the slits are slightly divergent. Moreover the holes are preferably coincident even if they might be of different sizes or slightly offset one another.

The invention claimed is:

1. In a pre-shaped, self-blocking reinforcement parietal prosthesis (1) for inguinal hernioplastic operations close to the spermatic cord (13), said prosthesis (1) having an elongated form and extending along a longitudinal axis (A1); the improvements of the prosthesis comprising:
   a first and a second superimposed layer (3, 4) of mesh of polypropylene material (2) respectively provided with a first and a second holes (5, 8) defining an aperture for accommodating the spermatic cord (13), with a first and second outer edges (6, 9) and with a first and second slits (7, 10) which connect respectively the first and the second holes (5, 8) to the first and second outer edges (6, 9);
   wherein the first and second slits (7, 10) extend from opposite sides with respect to said longitudinal axis (A1);
   wherein the first and the second layers (3, 4) are of different sizes so as to be partially superimposed; and the first layer (3) is partially joined to the second layer (4) together along two rectilinear portions (6c, 9c) of the first and second outer edges (6, 9) and substantially transversal to said longitudinal axis (A1) and along respective segments (11, 12) of the first and second outer edges (6, 9) and adjacent to said two rectilinear portions (6c, 9c);
   each of said portions being less than half the length of either of said outer edges (6, 9); wherein said prosthesis presents a second axis (A2) transversal to the first longitudinal axis (A1) and passing through said first and second holes (5, 8), said first and second layers (3, 4) being joined together on a same side with respect to the transversal axis (A2) only.

2. Prosthesis according to claim 1, wherein the first and the second slits (7, 10) lie on respective lines, which are essentially parallel.

3. Prosthesis according to claim 1, wherein said first and second slits (7, 10) are substantially transversal to said longitudinal axis (A1).

4. Prosthesis according to claim 1, wherein said first and second slits (7, 10) are aligned one another.

5. Prosthesis according to claim 1, wherein the first and the second outer edges (6, 9) are partly coincident.

6. Prosthesis according to claim 1, wherein the first and the second holes (5, 8) are substantially coincident.

7. In a pre-shaped, self-blocking reinforcement parietal prosthesis (1) for inguinal hemioplastic operations close to the spermatic cord (13), said prosthesis (1) having an elongated form and extending along a longitudinal axis (A1); wherein the improvements of the prosthesis comprises a first and a second layers (3, 4) made of a mesh of polypropylene material (2) respectively provided with a first and a second holes (5, 8) defining an aperture for accommodating the spermatic cord (13); wherein the prosthesis is made from a blank (14), which is folded so as to superimpose the first and the second layers (3, 4) and so that the first and the second holes (5, 8) be substantially coincident; wherein the first and the second layers (3, 4) are of different sizes so as to be partially superimposed; and the first layer (3) is partially joined to the second layer (4) along two rectilinear portions (6c, 9c) of the first and second outer edges (6, 9) and substantially transversal to said longitudinal axis (A1); each of said portions being less than half the length of either of said outer edges (6, 9); wherein said prosthesis presents a second axis (A2) transversal to the first longitudinal axis (A1) and passing through said first and second holes (5, 8), said first and second layers (3, 4) being joined together on a same side with respect to the transversal axis (A2) only.

8. In a method of production of a pre-shaped, self-blocking reinforcement parietal prosthesis for inguinal hernioplastic operations close to the spermatic cord (13), said prosthesis (1) having an elongated form and extending along a longitudinal axis (A1); wherein the prosthesis comprises a first and a second superimposed layers (3, 4) made of a mesh of polypropylene material (2) respectively provided with a first and a second holes (5, 8) defining an aperture for accommodating the spermatic cord (13), with a first and second outer edges (6, 9) and with a first and second slits (7, 10) which connect respectively the first and the second holes (5, 8) to the first and second outer edges (6, 9); the first and second slits (7, 10) extending from opposite sides with respect to said longitudinal axis (A1); the improvements of the method comprising the steps of:
   cutting a blank (14) extending along said longitudinal axis (A1) from a sheet made of a mesh of polypropylene material for surgery, said blank comprising the first and second layers (3, 4) in a flat planar configuration;
   making the first hole (5) in said blank (14) and the first slit (7) which connects said first hole (5) with the first outer edge (6) of the blank (14);
   making the second hole (8) in said blank (14) and the second slit (10) which connects said second hole (8) with the second outer edge (9) of the blank (14) on the side opposite to the first slit (7) with respect to the longitudinal axis (A1);
   folding the blank (14) substantially about two rectilinear portions (6c, 9c) of the first and second outer edge (6, 9) perpendicular to the longitudinal axis (A1) so as to superimpose the first and the second layers (3, 4) and to arrange the first and the second holes (5, 8) aligned with each other to define the aperture for said spermatic cord (13); and
   joining the first and second layers (3, 4) along two segments (11, 12) of the first and second outer edges (6, 9) and adjacent to the two rectilinear portions (6c, 9c).

* * * * *